United States Patent [19]
Kurdikar et al.

[11] Patent Number: 6,043,063
[45] Date of Patent: Mar. 28, 2000

[54] METHODS OF PHA EXTRACTION AND RECOVERY USING NON-HALOGENATED SOLVENTS

[75] Inventors: Devdatt L. Kurdikar, Maryland Heights; Fred E. Strauser, St. Charles; A. John Solodar, University City; Mark D. Paster; Jawed Asrar, both of Chesterfield, all of Mo.

[73] Assignee: Monsanto Company, St. Louis, Mo.

[21] Appl. No.: 09/060,121

[22] Filed: Apr. 14, 1998

Related U.S. Application Data

[60] Provisional application No. 60/043,017, Apr. 15, 1997.

[51] Int. Cl.[7] .................... C12P 7/42; C12P 7/62; C12N 1/20; C08G 63/06
[52] U.S. Cl. .................... 435/135; 203/14; 203/67; 210/767; 210/768; 210/787; 435/134; 435/146; 528/354; 528/361; 528/491; 528/492; 528/501
[58] Field of Search .................... 435/135, 134, 435/146; 528/491, 492, 501, 354, 361; 203/14, 67; 210/767, 768, 787

[56] References Cited

U.S. PATENT DOCUMENTS

| | | | |
|---|---|---|---|
| 4,205,162 | 5/1980 | Herscovici | 528/499 |
| 4,562,245 | 12/1985 | Stageman | 528/361 |
| 4,705,604 | 11/1987 | Vanlautem et al. | 203/67 |
| 4,968,611 | 11/1990 | Transsnig et al. | 435/135 |
| 5,213,976 | 5/1993 | Blauhut et al. | 435/135 |
| 5,422,257 | 6/1995 | Ohleyer | 435/135 |
| 5,496,923 | 3/1996 | Suizu et al. | 528/501 |
| 5,536,419 | 7/1996 | Esalona et al. | 210/767 |
| 5,821,299 | 10/1998 | Noda | 435/135 |

FOREIGN PATENT DOCUMENTS

| | | | |
|---|---|---|---|
| 9 302312-0 | 2/1995 | Brazil | C12P 7/62 |
| 0 124 309 | 11/1984 | European Pat. Off. | C12P 7/62 |
| 0 452 111 | 10/1991 | European Pat. Off. | C08G 63/90 |
| 0 707 024 | 4/1996 | European Pat. Off. | C08G 63/90 |
| 195 33 459 | 11/1996 | Germany | C08G 63/89 |
| 1 568 719 | 6/1980 | United Kingdom | C08G 63/72 |
| 94/10289 | 5/1994 | WIPO | C12N 1/08 |
| 95/33064 | 12/1995 | WIPO | C12P 7/62 |
| 95/33065 | 12/1995 | WIPO | C12P 7/62 |
| 96/06179 | 2/1996 | WIPO | C12P 7/62 |
| 97/07229 | 2/1997 | WIPO | C12P 7/62 |
| 97/07230 | 2/1997 | WIPO | C12P 7/62 |
| 97/08931 | 3/1997 | WIPO . | |
| 97/15681 | 5/1997 | WIPO | C12P 7/62 |

*Primary Examiner*—Herbert J. Lilling
*Attorney, Agent, or Firm*—Jon H. Beusen; Arnold White & Durkee

[57] ABSTRACT

Polyhydroxyalkanoate (PHA) polyester is extracted from biomass by dissolving the PHA in a non-halogenated solvent which comprises a PHA-good solvent or a mixture thereof. Suitable PHA-good solvents can be selected from the disclosed alcohols, esters, amides and ketones. The PHA can be recovered, for example, by cooling, by solvent evaporation, or by addition of a PHA-poor solvent, wherein the PHA-poor solvent preferably dissolves less than about 1% (w/v) of the PHA at a temperature below the solvent boiling point. Preferred PHA types for use in the invention are poly(hydroxybutyrate-co-hydroxyvalerate), poly(3-hydroxybutyrate-co-4-hydroxybutyrate), and polymers/copolymers of hydroxyterminated polyhydroxybutyrate.

63 Claims, No Drawings

METHODS OF PHA EXTRACTION AND RECOVERY USING NON-HALOGENATED SOLVENTS

This application is based on Provisional Application Ser. No. 60/043,017, filed Apr. 15, 1997.

BACKGROUND OF THE INVENTION

This invention relates to a process for the extraction and recovery of polyhydroxyalkanoate (PHA) from biomass.

There has been considerable interest in recent years in the use of biodegradable polymers to address concerns over plastic waste accumulation. The potential worldwide market for biodegradable polymers is enormous. Some of the markets and applications most amenable to the use of such biopolymers involve those having single, short use applications, including packaging, personal hygiene, garbage bags, and others. These applications, although poorly suited for recycling, are ideally suited for biodegradation through composting.

PHA biopolymers are thermoplastic polyesters produced by numerous microorganisms in response to nutrient limitation. The commercial potential for PHA spans many industries, and is derived primarily from certain advantageous properties which distinguish PHA polymers from petrochemical-derived polymers, namely excellent biodegradability and natural renewability. The success of PHA as a viable alternative to petrochemical-derived polymers, however, will depend upon the design and implementation of efficient and selective means of PHA production and recovery.

An improved understanding of the biology of PHA biosynthetic pathways has allowed for the use of microbial organisms, both natural and recombinant, and more recently plant cells, to produce significant quantities of PHA. Although such approaches have identified promising routes to PHA production, there remain obstacles to efficient and cost-effective PHA recovery from source materials at a useful level of quality and purity. Much of the effort directed to identifying methods for recovery of PHA have focused on recovery from bacterial sources using halogenated hydrocarbon solvents. The environmental implications and human toxicities associated with halogenated compounds, however, have created a need for separation processes which utilize PHA solvents with more benign properties.

SUMMARY OF THE INVENTION

In accordance with a first aspect of the present invention, there is provided a method of recovering PHA from biomass comprising:

providing biomass containing PHA;

dissolving the PHA with a non-halogenated solvent to produce a PHA-enriched solvent and residual biomass materials;

separating the residual biomass materials from the PHA-enriched solvent; and recovering the PHA from the PHA-enriched solvent.

The PHA is dissolved with solvents, hereinafter referred to as PHA-good solvents, typically selected from the group consisting of cyclic and acyclic (linear and branched) $R'$—OH alcohols where $R'=C_4–C_{10}$, cyclic and acyclic $R''$—COOR''' esters where $R''=H$ or $C_1–C_6$ and $R'''=C_1–C_7$, cyclic and acyclic $R''$—COOR''' esters where $R''=H$ or $C_1–C_6$ and $R'''=C_1–C_7$ and wherein at least one oxygen is substituted for at least one carbon in $R''$ or $R'''$, cyclic and acyclic $R^1$—CON—$(R^2)_2$ amides where $R^1=H$ or $C_1–C_6$ and $R^2=C_1–C_6$, and cyclic and acyclic $R^3$—CO—$R^4$ ketones where $R^3=C_1–C_6$ and $R^4=C_1–C_6$.

The PHA polymers most preferred for use in this invention include poly(hydroxybutyrate-co-hydroxyvalerate) copolymers (PHBV), poly(3-hydroxybutyrate-co-4-hydroxybutyrate) copolymers (3HB4HB), and hydroxyterminated polymers and copolymers of polyhydoxybutyrate (PHB-OH).

Therefore, in one preferred embodiment of this aspect of the invention the PHA is PHBV, and the PHA-good solvent is selected from the group consisting of butyl acetate, isobutyl acetate, ethyl lactate, isoamyl acetate, benzyl acetate, 2-methoxy ethyl acetate, tetrahydrofurfuryl acetate, propyl propionate, butyl propionate, pentyl propionate, butyl butyrate, isobutyl isobutyrate, ethyl butyrate, ethyl valerate, methyl valerate, benzyl benzoate, methyl benzoate, dimethyl succinate, dimethyl glutarate, dimethyl adipate, isobutyl alcohol, 1-butanol, 2-methyl-1-butanol, 3-methyl-1 butanol, 1-pentanol, 3-pentanol, amyl alcohol, allyl alcohol, hexanol, heptanol, octanol, cyclohexanol, 2-ethylhexanol, tetrahydrofurfuryl alcohol, furfuryl alcohol, benzyl alcohol, 2-furaldehyde, methyl isobutyl ketone, methyl ethyl ketone, g-butyrolactone, methyl n-amyl ketone, 5-methyl-2-hexanone, ethyl benzene, 1,3-dimethoxybenzene, cumene, benzaldehyde, 1,2-propanediol, 1,2-diaminopropane, ethylene glycol diethyl ether, 1,2,3-trimethylbenzene, 1,2,4-trimethylbenzene, 1,3-dioxane, 1,4-dioxane, 1-nitropropane, toluene-2,4-diisocyanate, acetic acid, acrylic acid, acetic anhydride, alpha-methylstyrene, acetophenone, toluene, ethylene glycol diacetate, dimethyl sulfoxide, dimethyl acetamide, dimethyl formamide and propylene carbonate.

In another preferred embodiment of this aspect of the invention the PHA is 3HB/4HB copolymer and the PHA-good solvent is selected from the group consisting of ethyl butyrate, propyl propionate, butyl acetate, butyl propionate, tetrahydrofurfuryl acetate, methyl propionate, methyl n-valerate, ethyl valerate, 1-butanol, 2-methyl-1-butanol, 3-methyl-1-butanol, 1-pentanol, 3-pentanol, amyl alcohol, 1-hexanol, ethylene glycol diacetate, tetrahydrofurfuryl alcohol, methyl amyl ketone, methyl isobutyl ketone, acetophenone, 1,2-diaminopropane, acetic anhydride, alpha-methyl styrene, dimethyl sulfoxide, propylene carbonate and 1,2,3-trimethyl benzene, dimethyl acetamide and dimethyl formamide.

In another preferred embodiment of this aspect of the invention the PHA is a polymer or copolymer of hydroxy-terminated PHB and the PHA-good solvent is selected from the group consisting of butyl propionate, tetrahydrofurfuryl acetate, methyl n-valerate, amyl alcohol, 1-hexanol, ethylene glycol diacetate, tetrahydrofurfuryl alcohol, acetophenone, methyl amyl ketone, 1,2-diaminopropane, acetic anhydride, alpha-methyl styrene, dimethyl sulfoxide, propylene carbonate, 1,2,3-trimethyl benzene, dimethyl acetamide and dimethyl formamide.

In accordance with a further aspect of the present invention, there is provided a method of recovering PHA from biomass comprising:

providing biomass containing PHA;

dissolving the PHA with a non-halogenated PHA-good solvent to produce a PHA-enriched solvent and residual biomass materials;

separating the residual biomass materials from the PHA-enriched solvent;

precipitating PHA polymer from the PHA-enriched solvent by adding a PHA-poor solvent; and recovering the precipitated PHA polymer.

A PHA-poor solvent useful in precipitating PHA according to the present invention comprises a non-halogenated solvent which preferably dissolves less than about 1% (w/v) of the PHA being extracted at temperatures less than the solvent boiling point. The PHA-poor solvent can be miscible or immiscible with the PHA-good solvent(s) used. Suitable PHA-poor solvents can include water, $R_1$—OH alcohols and $R_2$—COOR$_3$ esters where $R_1=C_1-C_4$, $R_2$=H or $C_1-C_3$, and $R_3=C_1-C_5$, and $C_5-C_{16}$ alkanes. Examples of preferred PHA-poor solvents include methanol, ethanol, n-propanol, iso-propanol, heptane, octane, and hexadecane.

In accordance with a further aspect of the present invention, there is provided a method of recovering PHA from oil-bearing seeds comprising:

providing seeds containing PHA;

co-dissolving PHA and oil to produce a PHA-enriched solvent/oil mixture and residual biomass materials;

separating the residual biomass materials from the PHA-enriched solvent/oil mixture; and separating PHA polymer from the PHA-enriched solvent/oil mixture.

Solvents useful in this aspect of the invention can include R'—OH alcohols where $R'=C_4-C_{10}$. A particularly preferred solvent is an amyl alcohol mixed isomeric solution comprising 1-pentanol, 2-methyl-1-butanol, and 3-methyl-1-butanol.

DESCRIPTION OF ILLUSTRATIVE EMBODIMENTS

The embodiments disclosed herein relate to novel methods for the extraction and recovery of PHA polymer from biomass materials, wherein the biomass materials are derived from PHA-producing plants or PHA-producing microorganisms.

There have been a number of reports describing the solvent extraction of PHB homopolymer from biomass sources, primarily from PHB-producing microorganisms. However, in attempting to apply these teachings to the solvent-based extraction of other PHA types, we have found that PHB solubility is in fact poor in most non-halogenated solvents, particularly under conditions desired for commercial scale processing and extraction of PHA. In addition, we have found that solvents which are effective for solubilizing one PHA type are not necessarily effective for solubilizing all PHA types.

The methods of the present invention are applicable to the recovery of PHA polymers produced by plant or microbial organisms either naturally or through genetic engineering, or PHAs that are synthetically produced. PHA is a polymer made from repeating units having the following general structure:

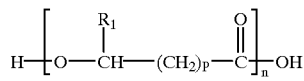

wherein $R_1$ is preferably an H, alkyl, or alkenyl; p is 0, 1, 2, or 3; and n is an integer. PHA can consist entirely of a single monomeric repeating unit, in which case it is referred to as a homopolymer. For example, polyhydroxybutyrate (PHB) homopolymer has repeating monomeric units wherein $R_1=C_1$ alkyl, and p=1. Copolymers, in contrast, contain two different types of monomeric units. PHBV, for example, is a copolymer containing polyhydroxybutyrate and polyhydroxyvalerate ($R_1=C_2$ alkyl, and p=1) units. Another copolymer of interest contains 3-hydroxybutyrate and 4-hydroxybutyrate units (P3HB4HB). When three different types of repeating units are present the polymer is referred to as a terpolymer.

The methods disclosed herein are also be applicable to the recovery of PHA which has been modified in a plant or microbial organism to provide improved or beneficial properties. In particular, the methods are useful for the extraction and recovery of PHAs modified to contain hydroxy-terminated end groups. Hydroxyterminated PHAs are useful in the production of graft, random and block polymers and copolymers with unique and improved properties, as disclosed in U.S. provisional application Ser. No. 60\044,042, filed Apr. 21, 1997.

This invention is applicable to PHA recovery from essentially any plant type. For example, the plants can be monocots or dicots and suitable plant source materials can be derived from roots, stems, leaves, flowers, fruits, seeds etc. Some of the preferred biomass sources for use in this invention include corn stover, switchgrass, sugarcane and oilseed crops.

For oilseed crops, such as canola, rapeseed, soybean, safflower, and sunflower, genetic engineering can produce plants in which PHA is biosynthetically produced in the seeds of the crops. In order to recover PHA polymer from the seeds of such plants, it is necessary to separate the polymer from the vegetable oil and oilseed meal also present. The seeds are typically processed by conventional methods. For example they can be crushed and/or dehulled and/or protein extracted prior to PHA extraction, although not necessarily in this order. The oilseed meal which is separated from the PHA-enriched solvent may be further processed and utilized as animal feed, or, utilized as an additive in animal feed.

The disclosed solvents are useful for the extraction and recovery of PHA polymer from oil-bearing seeds which comprise a mixture of vegetable oil, oilseed meal, and PHA. The vegetable oil from the seeds can be extracted, for example using hexane or another suitable solvent, and the oil-enriched solvent mixture can be separated from the PHA-meal mixture. The PHA in the PHA-meal mixture can then be selectively solubilized using one or more of the disclosed solvents, and PHA polymer can be recovered by conventional approaches such as cooling or solvent evaporation. Alternatively, methods are provided whereby PHA can be precipitated from the PHA-enriched solvent mixture using the disclosed non-halogenated PHA-poor solvents.

The separation of the meal from the PHA solution via filtration can be problematic because the meal often has a consistency that makes it difficult for the PHA solution to permeate through the meal. As a result, the filter can become plugged. It may be preferred to wash the meal with water or hexane prior to the PHA dissolution step. We have found that this markedly improves the filtration characteristics of the meal.

Methods are also provided for co-dissolving PHA and oil from a mixture of oil, oilseed meal, and PHA, separating the PHA-enriched solvent/oil mixture from the oilseed meal and any other residual biomass components, and precipitating PHA from the PHA-enriched solvent/oil mixture.

PHA-good solvents useful in this invention are typically selected from cyclic and acyclic (linear and branched) R'—OH alcohols where $R'=C_4-C_{10}$, cyclic and acyclic R"—COOR''' esters where R"=H or $C_1-C_6$ and $R'''=C_1-C_7$, cyclic and acyclic R"—COOR''' esters where R"=H or $C_1-C_6$ and $R'''=C_1-C_7$ and wherein at least one oxygen is substituted for at least one carbon in R" or R''', cyclic and acyclic $R^1$—CON—$(R^2)_2$ amides where $R^1$=H or $C_1-C_6$ and $R^2=C_1-C_6$, and cyclic and acyclic $R^3$—CO—$R^4$ ketones where $R^3=C_1-C_6$ and $R^4=C_1-C_6$ In one preferred embodiment of the invention the PHA is PHBV and the PHA-good solvent is selected from the group consisting of butyl acetate, isobutyl acetate, ethyl lactate, isoamyl acetate, benzyl acetate, 2-methoxy ethyl acetate, tetrahydrofurfuryl acetate, propyl propionate, butyl propionate, pentyl propionate, butyl butyrate, isobutyl isobutyrate, ethyl butyrate, ethyl valerate, methyl valerate, benzyl benzoate, methyl benzoate, dimethyl succinate, dimethyl glutarate, dimethyl adipate, isobutyl alcohol, 1-butanol, 2-methyl-1-butanol, 3-methyl-1 butanol, 1-pentanol, 3-pentanol, amyl alcohol, allyl alcohol, hexanol, heptanol, octanol, cyclohexanol, 2-ethylhexanol, tetrahydrofurfuryl alcohol, furfuryl alcohol, benzyl alcohol, 2-furaldehyde, methyl isobutyl ketone, methyl ethyl ketone, g-butyrolactone, methyl n-amyl ketone, 5-methyl-2-hexanone, ethyl benzene, 1,3-dimethoxybenzene, cumene, benzaldehyde, 1,2-propanediol, 1,2-diaminopropane, ethylene glycol diethyl ether, 1,2,3-trimethylbenzene, 1,2,4-trimethylbenzene, 1,3-dioxane, 1,4-dioxane, 1-nitropropane, toluene-2,4-diisocyanate, acetic acid, acrylic acid, acetic anhydride, alpha-methylstyrene, acetophenone, toluene, ethylene glycol diacetate, dimethyl sulfoxide, dimethyl acetamide, dimethyl formamide and propylene carbonate.

In another preferred embodiment of the invention the PHA is P3HB4HB copolymer and the PHA-good solvent is selected from the group consisting of ethyl butyrate, propyl propionate, butyl acetate, butyl propionate, tetrahydrofurfuryl acetate, methyl propionate, methyl n-valerate, ethyl valerate, 1-butanol, 2-methyl-1-butanol, 3-methyl-1-butanol, 1-pentanol, 3-pentanol, amyl alcohol, 1-hexanol, ethylene glycol diacetate, tetrahydrofurfuryl alcohol, methyl amyl ketone, methyl isobutyl ketone, acetophenone, 1,2-diaminopropane, acetic anhydride, alpha-methyl styrene, dimethyl sulfoxide, propylene carbonate and 1,2,3-trimethyl benzene, dimethyl acetamide and dimethyl formamide.

In another preferred embodiment of the invention the PHA is a polymer or copolymer of hydroxyterminated PHB and the PHA-good solvent is selected from the group consisting of butyl propionate, tetrahydrofurfuryl acetate, methyl n-valerate, amyl alcohol, 1-hexanol, ethylene glycol diacetate, tetrahydrofurfuryl alcohol, acetophenone, methyl amyl ketone, 1,2-diaminopropane, acetic anhydride, alpha-methyl styrene, dimethyl sulfoxide, propylene carbonate and 1,2,3-trimethyl benzene, dimethyl acetamide and dimethyl formamide.

PHA is generally dissolved at temperatures between 25° C. and 180° C., preferably between 50° C. and 160° C., and more preferably between 90° C. and 160° C. Temperature considerations are important from a commercial standpoint, since the temperature at which a polymer is dissolved, and the time required for adequate dissolution, can impact capital costs and product quality. Selection of operating conditions (mainly time and temperature of extraction) should be dependent to some extent on the particular solvent employed. It is advantageous where possible to use solvents and processing parameters which minimize both equipment costs and polymer exposure to adverse conditions which can cause polymer degradation.

The PHA concentration in the PHA-enriched solvent is typically between 1% and 40% w/v, preferably from about 2 to 20% w/v.

When using methods of solvent-based PHA recovery from biomass in general, and from oil-bearing seeds in particular, meal components/color bodies frequently leach into the solvent, resulting in a PHA-enriched solvent which is brown/yellow in color. PHA recovery from the PHA-enriched solvent by evaporating the solvent to dryness then results in polymer which is brown/yellow in color. For many applications a white or off-white colored polymer is desired to maximize commercial potential and marketability. In this regard, the color characteristic of the recovered polymer is an important measure of polymer quality. Furthermore, the presence of these meal components/color bodies may contribute to sub-optimal polymer characteristics.

Therefore, to minimize any negative effects of meal components/color bodies on polymer properties, and to reduce objectionable color in recovered PHA, a bleaching/decolorization step is provided wherein most of the meal components/color bodies are adsorbed, for example using activated carbon or clay, or in some other way separated from the polymer solution. As a result, polymer having a desirable white or off-white color can be obtained. A similar decolorization step may be necessary or desired when PHA is recovered from a bacterial source. Furthermore, the decolorization step can be included in most solvent-based extraction strategies, and is not limited for use only in conjunction with the solvents disclosed herein.

PHA can be recovered from a PHA-enriched solvent, for example by solvent evaporation. The solvent can be partially evaporated, or completely evaporated to dryness. Alternatively, the PHA can be recovered by reducing the temperature of the PHA-enriched solvent until PHA precipitation has occurred. In many cases, cooling the PHA-enriched solvent results in the formation of a gel. Polymer in this form can be recovered by compressing the gel, thereby producing flakes of polymer which have reduced solvent content compared to the gel. Most of the remaining solvent can be removed from the polymer flakes by increasing the temperature of the flakes, optionally under vacuum, to a point which approaches or exceeds the boiling point of the solvent.

In a further embodiment of the present invention, the precipitation of PHA polymer from PHA-enriched solvent can be accomplished by addition of an appropriate PHA-poor solvent. The addition of a PHA-poor solvent reduces the solubility of PHA in at least one phase of the resulting mixture, thereby contributing to efficient precipitation of PHA polymer without impairing polymer purity and quality. Preferred PHA-poor solvents as disclosed herein are non-halogenated solvents which dissolves less than about 1% w/v (i.e. 1 g PHA in 100 cc solvent) of the PHA at temperatures below their boiling points.

The PHA can be dissolved with a single PHA-good solvent, or a mixture of one or more PHA-good solvents, to produce the PHA-enriched solvent. The PHA-poor solvent used to precipitate PHA from a PHA-enriched solvent can be a mixture of one or more PHA-poor solvents, or can be a mixture comprising a PHA-good solvent and a PHA-poor solvent. The PHA dissolved in the PHA-enriched solvent can be concentrated, for example by partial evaporation of the PHA-good solvent, prior to the addition of the PHA-poor solvent.

Generally, when a PHA-poor solvent is used to precipitate PHA from a PHA-enriched solvent mixture, the recovered polymer is white or off-white in color. Thus, most of the meal components/color bodies remain in the solvent solution when using this approach. If desired, the color (i.e. whiteness) of the polymer may be further improved in a number of ways. For example, the polymer can be thoroughly washed before drying. In addition, the polymer can be introduced into the PHA-poor solvent in a form (e.g. as droplets) so that the meal components/color bodies more effectively stay in solution rather than getting entrapped in the precipitated polymer. The PHA-enriched solvent may optionally be treated with activated clay or carbon prior to the addition of the PHA-poor solvent.

The PHA-poor solvent can be immiscible (i.e., less than about 10% solubility) with the PHA-good solvent. In this case, some of the precipitation of PHA polymer occurs at the interface of the PHA-good solvent and PHA-poor solvent. Alternatively, the PHA-poor solvent can be miscible (i.e., greater than about 90% solubility) with the PHA-good solvent. The use of PHA-poor solvents allow for the precipitation of PHA polymer from a PHA-enriched solvent mixture such that the polymer precipitates while many of the meal components/color bodies remain in solution. The precipitated polymer may then be separated from the PHA-good solvent/PHA-poor solvent mixture by a conventional solid-liquid separation technique, for example by filtration or centrifugation. The precipitated polymer can be further washed if desired, and then dried.

Suitable PHA-poor solvents which are generally miscible with the disclosed PHA-good solvents include water, and $R_1$—OH alcohols, $R_2$—COOR$_3$ esters where $R_1=C_1-C_4$, $R_2$=H or $C_1-C_3$, and $R_3=C_1-C_5$, and linear or branched $C_5-C_{16}$ alkanes. Methanol, ethanol, n-propanol, isopropanol, heptane, octane, and hexadecane, for example, are particularly useful. Other non-halogenated PHA-poor solvents which have >90% solubility with the PHA-good solvent used are also expected to be suitable. PHA-poor solvents which are typically immiscible with many of the PHA-good solvents include water and other non-halogenated PHA-poor solvents which have less than about 10% solubility with the PHA-good solvent used.

It should be noted that PHA composition and morphology (polarity, presence or absence of crystallinity etc.) are determinants of polymer solubility characteristics. Generally, polymers with high crystallinity are more difficult to dissolve than those with low crystallinity. Furthermore, the thermal history of the polymer may also effect solubility. If the PHA has side chains, as the size of the chain increases the number of methylene groups in the polymer increases and therefore the polarity of the polymer changes. However, with a change in the size of the side chains, the crystallinity of the polymer is also effected which in turn effects the solubility characteristics. Such variables make it difficult to accurately predict PHA solubility from simple criteria, such as similarities in chemical architecture or matching of refractive indices, dielectric constants or solubility parameters.

Miscible and immiscible solvent pairs should be chosen appropriately. For example, water is miscible with DMF, ethyl lactate, and dimethyl acetamide, but has limited solubility in 1-pentanol, 2-methyl-1-butanol, and other PHA-good solvents.

In the case of the miscible PHA-good/PHA-poor solvent system, the PHA-good solvent and/or the PHA-poor solvent may be recovered, purified by distillation, liquid—liquid extraction, or some other separation method, and recycled, optionally after purification. In addition, the PHA-good solvent and the PHA-poor solvent can be separated in a manner such that most or all non-PHA plant material, if present, remains with the PHA-good solvent. Non-PHA plant material can be fully recovered, or concentrated in a PHA-good solvent stream, and added to residual plant materials separated from the PHA-enriched solvent.

In the case of the immiscible PHA-good /PHA-poor solvent system, the solvents can be phase separated, followed by purification of each phase if necessary or desired. These streams can be recycled or a purge stream can be taken off. Meal components/color bodies may be removed before the solvents are re-used.

In yet a further embodiment of the present invention, a method for PHA recovery from oil-bearing seeds is provided wherein PHA and oil are co-dissolved using a non-halogenated solvent and PHA is precipitated from the PHA-enriched solvent/oil mixture. Preferred solvents are selected from linear and branched R'—OH alcohols where R'=$C_4-C_{10}$. A most preferred solvent for use in this embodiment is an amyl alcohol mixed isomeric solution comprising 1-pentanol, 2-methyl-1-butanol, and 3-methyl-1-butanol. In practice, vegetable oil and the PHA are first solubilized to produce a PHA-enriched solvent/oil mixture. The PHA concentration in the PHA-enriched solvent/oil mixture is typically between 1% and 40% w/v. The PHA is typically dissolved at a temperature in the range of 25–180° C., preferably from 50–160° C., and more preferably from 90–160° C. The PHA-enriched solvent/oil mixture can be separated from residual biomass material (comprised primarily of oilseed meal) using conventional solid-liquid separation techniques. By reducing the temperature of the PHA-enriched solvent/oil mixture, PHA can be effectively precipitated from the solvent/oil mixture without the need for an oil extraction step. Precipitated PHA can then be separated from the solvent/oil mixture, and solvent can be separated from the oil, for example by solvent evaporation. Alternatively, the PHA-enriched solvent/oil mixture can be heated, optionally under vacuum, causing the solvent to evaporate. Due to the insolubility of PHA in oil, it precipitates out and can be recovered by conventional solid-liquid separation methods. Optionally, the solvent may be condensed, partially or completely purified, and recycled.

The following examples are included to demonstrate preferred embodiments of the invention. It should be appreciated by those of skill in the art that the techniques disclosed in the examples which follow represent discoveries by the inventors which function effectively in the practice of the invention, and thus can be considered to constitute examples of preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

For the PHB and PHBV solubility experiments described below, tests were generally performed by first preparing mixtures of appropriate concentration (1–12% w/v i.e. 1–12 g of PHA per 100 cc solvent) in the chosen solvent. This mixture was heated using a heating block in a test-tube up to a temperature near the boiling point of the solvent. (In some cases, when the boiling point of the solvent was above 130° C., the maximum temperature that the PHA/solvent mixture was heated to was 130° C.). The test-tube were occasionally vortexed and solubility was determined visually. If particulates were observed, the PHA was reported as insoluble. If a clear solution was observed, the PHA was reported as soluble.

A 1% w/v mixture was prepared by adding PHB or PHBV (12% HV) to butyl acetate in a test-tube. These mixtures were heated simultaneously on a heating block. Occasionally the test-tubes were vortexed and the appearance of the resulting solution was observed to check for solubility. At 115° C., the PHB mixture was removed from the heating block and vortexed. PHB solubility was not observed. As soon as the vortexing was completed, the PHB started settling at the bottom of the test-tube. At 124° C., the PHBV solution in butyl acetate appeared clear after vortexing, and was reported as soluble. In another experiment, a 1% w/v mixture of PHB in butyl acetate was heated in test-tube using a heating block to 124° C. PHB was again reported as insoluble.

EXAMPLE 2

A 1% w/v mixture of PHB in butyl propionate was prepared in a beaker which was then heated using a hot plate, with constant stirring. This mixture was maintained at 117–126° C. for 1 hour, then at 133–138° C. for another hour, and finally heated to 143° C. PHB solubility in butyl propionate was not observed.

A 1% w/v mixture of PHBV (8% HV) in butyl propionate was heated to 141° C. and maintained at that temperature for 30 minutes. Complete solubility of PHBV in butyl propionate was observed.

EXAMPLE 3

A 1% w/v mixture was prepared by adding PHB or PHBV (12% HV) to 1-pentanol, 3-pentanol, or 2-methyl-1-butanol in separate test-tubes. These mixtures were heated simultaneously using a heating block up to the temperature at which the solvent started boiling or the PHA went into solution, but not exceeding 130° C. The test-tubes were occasionally removed from the heating block, vortexed, and replaced on the heating block. Visual observations as to the solubility characteristics of the PHA were made. When the temperature reached 117° C., the PHB in 3-pentanol was insoluble, whereas the PHBV was soluble. At a temperature of 120° C., PHBV was observed to be soluble in 2-methyl-1-butanol, whereas PHB was observed to be insoluble at 125° C. PHBV was observed to be soluble in 1-pentanol at 130° C., however PHB was insoluble at the same temperature.

EXAMPLE 4

Mixtures of 4% w/v were prepared by adding PHB or PHBV (8% HV) to 1-hexanol. These mixtures were heated simultaneously on a heating block to a temperature of 124° C. During the heating, the test-tubes were occasionally removed from the heating block, vortexed, and replaced on the heating block. The PHBV was observed to have dissolved in 1-hexanol at 124° C., but the PHB was insoluble.

In another experiment, a 1% w/v mixture of PHB in 1-hexanol was prepared in a beaker which was then heated using a hot plate with continuous stirring. This mixture was maintained at 121–127° C. for 1 hour, then at 136–143° C. for another hour, and finally heated to 153° C. PHB solubility in 1-hexanol was not observed.

EXAMPLE 5

For P3HB4HB (11.6% 4HB) solubility tests, PHA/solvent mixtures of appropriate concentration (1–4% w/v i.e. 1–4 g PHA per 100 cc solvent) were prepared by adding PHA to the solvent being tested in a test-tube which also contained a small magnetic spinning bar for agitation. The test tube was placed in an oil bath maintained at the desired temperature while being stirred. If a clear solution was observed, the added amount of the PHA was reported as completely dissolved in the solvent. If solid PHA was still observed after maintaining the sample at the desired temperature for longer than 30 minutes, with ample agitation to stir up the PHA, the added amount of the PHA was reported as not completely dissolved.

For P3HB4HB (7% 4HB) solubility tests, mixtures of appropriate concentration (1–12% w/v i.e. 1–12 g of PHA per 100 cc solvent) were prepared in the chosen solvent. This mixture was heated using a heating block in a test-tube up to a temperature near the boiling point of the solvent. In some cases, when the boiling point of the solvent was above 130° C., the maximum temperature that the PHA/solvent mixture was heated to was 130° C. The test-tube were occasionally vortexed and solubility was determined visually. If particulates were observed, the PHA was reported as insoluble. If a clear solution was observed, the PHA was reported as soluble. The results are set forth below in Table 1:

TABLE 1

P3HB4HB SOLUBILITY

| % 4HB | Solvent name | Soluble | Conc. | Temp (C.) |
|---|---|---|---|---|
| 11.6 | ethyl butyrate | yes | 2.1 | 120 |
| 11.6 | propyl propionate | yes | 1.1 | 118 |
| 11.6 | propyl propionate | yes | 1 | 117 |
| 11.6 | butyl acetate | yes | 2 | 120 |
| 11.6 | butyl propionate | yes | 2.1 | 123 |
| 11.6 | tetrahydrofurfuryl acetate | yes | 2.1 | 121 |
| 11.6 | methyl propionate | yes | 1 | 75 |
| 11.6 | methyl n-valerate | yes | 1 | 115 |
| 11.6 | ethyl valerate | yes | 1 | 124 |
| 11.6 | 1-butanol | yes | 2.2 | 116 |
| 7 | 2-methyl-1-butanol | yes | 2 | 117 |
| 7 | 2-methyl-1-butanol | yes | 8 | 115–118 |
| 7 | 3-methyl-1-butanol | yes | 2 | 126 |
| 7 | 3-methyl-1-butanol | yes | 8 | 125 |
| 7 | 1-pentanol | yes | 2 | 126 |
| 7 | 1-pentanol | yes | 8 | 125 |
| 11.6 | 3-pentanol | yes | 1.1 | 115 |
| 11.6 | amyl alcohol | yes | 4.4 | 128 |
| 11.6 | 1-hexanol | yes | 2.2 | 134 |
| 11.6 | ethyl diacetate glycol | yes | 2 | 137 |
| 11.6 | tetrahydrofurfuryl alcohol | yes | 2.1 | 117 |
| 11.6 | methyl amyl ketone | yes | 1.4 | 120 |
| 11.6 | methyl isobutyl ketone | yes | 1.4 | 115 |
| 11.6 | acetophenone | yes | 2.1 | 110 |
| 11.6 | 1,2-diaminopropane | yes | 2.1 | 115 |
| 11.6 | acetic anhydride | yes | 2.1 | 116 |
| 11.6 | alpha-methyl styrene | yes | 2.1 | 126 |
| 11.6 | dimethyl sulfoxide | yes | 2.1 | 117 |
| 11.6 | propylene carbonate | yes | 2.1 | 110 |
| 11.6 | 1,2,3-trimethyl benzene | yes | 2.2 | 121 |
| 11.6 | dimethyl acetamide | yes | 1 | 90 |
| 11.6 | dimethyl formamide | yes | 1 | 90 |

EXAMPLE 6

For PHB-OH (hydroxyterminated PHB) solubility tests, PHA/solvent mixtures of appropriate concentration (1–4% w/v i.e. 1–4 g PHA per 100 cc solvent) were prepared by adding PHA to the solvent being tested in a test-tube which also contained a small magnetic spinning bar for agitation. The test tube was placed in an oil bath maintained at the desired temperature while being stirred. If a clear solution was observed, the PHA was reported as soluble. If solid PHA was still observed after maintaining the sample at the desired temperature for longer than 30 minutes, with ample agitation to mix the PHA, the PHA was reported as insoluble. The results are set forth below in Table 2:

TABLE 2

Hydroxyterminated PHB
90% hydroxytermination
Mw = 215000
Mn = 50000

| Solvent name | Soluble | Conc. | Temp (C.) |
|---|---|---|---|
| ethyl butyrate | no | 1 | 118 |
| propyl propionate | no | 1 | 122 |
| propyl propionate | no | 1 | 120 |
| butyl acetate | no | 1 | 123 |
| butyl propionate | yes | 4 | 138 |
| tetrahydrofurfuryl acetate | yes | 1 | 128 |
| methyl propionate | no | 1 | 75 |
| methyl n-valerate | yes | 1 | 123 |
| ethyl valerate | no | 1 | 140 |
| 1-butanol | no | 1 | 116 |
| 3-pentanol | no | 1 | 112 |
| amyl alcohol | yes | 3.5 | 130 |
| 1-hexanol | yes | 3.4 | 145 |
| ethyl diacetate glycol | yes | 4.1 | 143 |
| tetrahydrofurfuryl alcohol | yes | 1 | 127 |
| acetone | no | 1 | 56 |
| methyl isobutyl ketone | no | 1 | 115 |
| acetophenone | yes | 1 | 128 |
| methyl amyl ketone | yes | 1 | 138 |
| 1,2-diaminopropane | yes | 1 | 95 |
| acetic anhydride | yes | 1 | 130 |
| alpha-methy styrene | yes | 1.1 | 128 |
| dimethyl sulfoxide | yes | 1 | 120 |
| propylene carbonate | yes | 1.1 | 123 |
| 1,2,3-trimethyl benzene | yes | 1 | 142 |
| dimethyl acetamide | yes | 1 | 121 |
| dimethyl formamide | yes | 1 | 115 |

EXAMPLE 7

2-methyl-1-butanol was contacted with canola meal at 120–130° C. with stirring. The mixture was filtered to remove the meal. A solvent was collected which had an obvious brown/yellow discoloration. This solvent-extract was treated with 6.9 wt. % activated carbon (Norit A) for 30 minutes at 115° C. This treatment effectively removed most of the brown/yellow color from the solvent. UV absorption was decreased 75% at 220 nm and 94% at 335 nm as compared with the solvent prior to activated carbon treatment.

EXAMPLE 8

A mixture containing 75% dry canola meal and 25% PHBV (8%) was prepared. 4.977 g of this mixture was added to 50 cc of N,N-dimethyl formamide (DMF) being stirred and maintained at 85–92° C. After 15 minutes, stirring was turned off and the meal allowed to settle to the bottom. The polymer solution which was dark yellow/brown in color was then slowly decanted into 100 cc of deionized water maintained at approximately 60° C. under stirring. Precipitate was observed when the polymer solution in DMF contacted the water. After 15 minutes, the heat supply to the water was stopped and the water containing the precipitated polymer was allowed to cool to 40° C. The PHBV was recovered by filtration using a medium frit glass filter funnel. The polymer was further washed on the filter funnel with 70 cc of water. The filter funnel containing the PHA was dried in a vacuum (25 inches Hg) oven overnight at 45–50° C. Polymer recovery was 84.9% and the color of the polymer was off-white.

EXAMPLE 9

A mixture containing 75% dry canola meal and 25% PHBV (8% HV) was prepared. 5.385 g of this mixture was added to 100 cc of 2-methyl-1-butanol being maintained at 125–130° C. under agitation. After 15 minutes, the stirring and heating were stopped, and the meal was allowed to settle to the bottom of the flask. The 2-methyl-1-butanol solution containing the dissolved polymer was yellow/brown in color. This solution was slowly decanted into a beaker containing 200 cc of n-propanol maintained at room temperature under stirring. The temperature of this mixture rose to 47° C. upon addition of the hot polymer solution. This mixture was stirred for 35 minutes. The polymer was recovered by filtering through a medium frit glass filter funnel. The polymer was further washed by passing distilled water through the filter funnel. The polymer was then dried in a vacuum oven (25 inches Hg) overnight at 45–50° C.

EXAMPLE 10

A mixture containing 75% dry canola meal and 25% PHBV (8% HV) was prepared. 5 g of this mixture was added to 50 cc of 2-methyl-1-butanol at about 130° C. Upon addition, solution temperature dropped to 119° C., and was maintained in a range of 119° C.–126° C. for 25 minutes. The meal was allowed to settle for 3 minutes and the solution was decanted into 100 cc of water wherein a dark brown precipitate formed. To improve the color of the precipitate, it was washed with 500 cc of water while being vacuum filtered and was then allowed to sit in 300 cc of water for one hour. The mixture was blended in a Waring blender for 20 seconds, vacuum filtered, blended again in 200 cc of water for 3 minutes, and vacuum filtered again. The polymer was dried overnight under vacuum at 50° C. Upon drying, the polymer had an off white color.

EXAMPLE 11

A mixture containing 75% dry canola meal and 25% PHBV (8% HV) was prepared. 5 g of this mixture was added to 50 cc of 1-pentanol at 130° C. Upon addition, solution temperature dropped slightly but was adjusted and kept in a range of 119° C.–126° C. for approximately 30 minutes. The solution was filtered through a warm (about 90° C.) coarse glass filter funnel; the filtrate formed a gel on cooling. This gel was added with 20 cc of water to a blender that contained 100 cc deionized water. The material was mixed in the blender for 15 minutes and then filtered through a medium pore sized glass filter funnel. The filtrate was a two phase solution. The upper phase was slightly cloudy and pale yellow in color. The bottom phase was milky white. This two phase solution was re-filtered through a fine glass filter funnel. No additional precipitate was recovered and the appearance of the filtrate did not change. The medium filter and filter cake was dried overnight under vacuum at 50° C. The dried polymer was off white in color.

EXAMPLE 12

100 cc of 2-methyl-1-butanol was contacted with 30 g dry canola meal at 120–130° C. with stirring for 1 hour. The mixture was filtered and a yellow-colored solvent was collected. 25 cc of this yellow-colored solvent was heated to 120–130° C. and 2.007 g of PHBV (8% HV) were added to it. After the PHA had dissolved into the solvent, the polymer solution was added to a stirred mixture of 25 cc n-propanol and 25 cc of 2-methyl-1-butanol maintained at about 101° C. The temperature of the resulting solution rose to 106° C. As the solution cooled, cloudiness appeared at 101° C. and swollen polymer particles were observed at 72° C. The solution was cooled to 40° C. or less and then filtered under vacuum to remove as much of the liquid mixture as possible.

The recovered polymer was then washed with 37.5 cc of n-propanol in an open beaker with stirring. The polymer was again recovered by filtration and dried in a vacuum oven overnight at 50° C. The color of the dried PHA was white.

EXAMPLE 13

100 cc of 3-methyl-1-butanol (tech grade; 70–85% 3-methyl-1-butanol, remainder 2-methyl-1-butanol) was contacted with 30 g dry canola meal at 120–130° C. with stirring for 1 hour. The mixture was filtered to remove the meal and a yellow-colored solvent was collected. 25 cc of this yellow-colored solvent was heated to 120° C. and 2.003 g of PHBV (8% HV) were added to it. After the PHA had dissolved into the solvent, the polymer solution was then added to a stirred mixture of 25 cc of n-propanol and 25 cc of 3-methyl-1-butanol (tech grade) maintained at around 101° C. The temperature of the resulting solution increased to 109° C. As the solution cooled, cloudiness appeared at 82° C. and swollen polymer particles were obtained at 70° C. The solution was cooled to 40° C. or less and then filtered using vacuum to remove as much liquid as possible. The recovered polymer was then washed with 37.5 cc n-propanol in an open beaker with stirring. The polymer was again recovered by filtration and dried in a vacuum oven overnight at 50° C. The color of the dried PHA was white.

EXAMPLE 14

20 g of dry, ground, stover from a corn plant genetically engineered to produce 15% PHA (PHBV; 8% HV) is contacted with 100 cc of amyl alcohol in a stirred vessel at 130° C. for 1 hour. The mixture is filtered through a warm (about 90° C.) coarse glass filter funnel to remove the undissolved biomass and the PHA solution is collected. This polymer solution is added to a stirred mixture of 100 cc of n-propanol and 100 cc of 3-methyl-1-butanol (tech grade) maintained at around 100° C. The resulting solution is allowed to cool to 50° C. and then filtered using vacuum to remove as much liquid as possible. The recovered polymer is then washed with 150 cc n-propanol in an open beaker with stirring. The polymer is recovered by filtration and dried in a vacuum oven overnight at 50° C.

All of the methods disclosed and claimed herein can be made and executed without undue experimentation in light of the present disclosure. While the compositions and methods of this invention have been described in terms of specific embodiments, it will be apparent to those of skill in the art that variations may be applied to the methods and in the steps or in the sequence of steps of the methods described herein without departing from the concept, spirit and scope of the invention. More specifically, it will be apparent that other solvents may be substituted for those described herein while the same or similar results would be achieved. All such similar substitutes and modifications apparent to those skilled in the art are deemed to be within the spirit, scope and concept of the invention as defined by the appended claims.

What is claimed is:

1. A method of recovering polyhydroxyalkanoate (PHA) from biomass comprising:
   providing biomass containing PHA;
   dissolving PHA with a solvent to produce PHA-enriched solvent and residual biomass materials;
   separating the residual biomass materials from the PHA-enriched solvent; and
   recovering PHA polymer from the PHA-enriched solvent, wherein:
   the PHA is selected from the group consisting of poly (hydroxybutyrate-co-hydroxyvalerate) (PHBV), poly (3-hydroxybutyrate-co-4-hydroxybutyrate) (3HB4HB), and polymers and copolymers of hydroxy-terminated polyhydroxybutyrate (PHB-OH); and
   when the PHA is 3HB4HB or PHB-OH, the solvent is selected from the group consisting of: cyclic and acyclic R'—OH alcohols where R'=$C_4$–$C_{10}$, dimethyl glutarate, dimethyl adipate, isobutyl acetate, ethyl lactate, isoamyl acetate, benzyl acetate, 2-methoxy ethyl acetate, tetrahydrofurfuryl acetate, propyl propionate, pentyl propionate, butyl butyrate, isobutyl isobutyrate, ethyl butyrate, ethyl valerate, methyl valerate, benzyl benzoate, methyl benzoate, methyl propionate, allyl alcohol, tetrahydrofurfuryl alcohol, furfuryl alcohol, ethyl benzene, 1,3-dimethoxybenzene, cumene, benzaldehyde, 2-furaldehyde, 1,2-propanediol, 1,2-diaminopropane, ethylene glycol diethyl ether, 1,2,3-trimethylbenzene, 1,2,4-trimethylbenzene, 1,3-dioxane, 1-nitropropane, toluene-2,4-diisocyanate, acetic acid, acrylic acid, acetic anhydride, methyl isobutyl ketone, methyl n-amyl ketone, 5-methyl-2-hexanone, acetophenone, dimethyl acetamide, alpha-methyl styrene, and propylene carbonate and when the PHA is PHBV, the solvent is selected from the group consisting of cumene, benzaldehyde, 2-furaldehyde, toluene-2,4-diisocyanate, alpha-methylstyrene, acetic acid, acrylic acid, acetic anhydride, 1,2-diaminopropane, 1-nitropropane, and an amyl alcohol mixed isomeric solution comprising 1-pentanol, 2-methyl-1-butanol, and 3-methyl-1-butanol.

2. The method of claim 1, wherein the PHA is PHBV, and the solvent is selected from the group consisting of cumene, benzaldehyde, 2-furaldehyde, toluene-2,4-diisocyanate, alpha-methylstyrene, acetic acid, acrylic acid, acetic anhydride, 1,2-diaminopropane 1-nitropropane, and an amyl alcohol mixed isomeric solution comprising 1-pentanol, 2-methyl-1-butanol, and 3-methyl-1-butanol.

3. The method of claim 1, wherein the PHA is P3HB4HB copolymer and the solvent is selected from the group consisting of ethyl butyrate, propyl propionate, tetrahydrofurfuryl acetate, methyl propionate, methyl n-valerate, ethyl valerate, 1-butanol, 2-methyl-1-butanol, 3-methyl-1-butanol, 1-pentanol, 3-pentanol, amyl alcohol, 1-hexanol, tetrahydrofurfuryl alcohol, methyl amyl ketone, methyl isobutyl ketone, acetophenone, 1,2-diaminopropane, acetic anhydride, alpha-methyl styrene, propylene carbonate, and 1,2,3-trimethyl benzene, and dimethyl acetamide.

4. The method of claim 1, wherein the PHA is a polymer or copolymer of hydroxyterminated PHB and the solvent is selected from the group consisting of tetrahydrofurfuryl acetate, methyl n-valerate, amyl alcohol, 1-hexanol, tetrahydrofurfuryl alcohol, acetophenone, methyl amyl ketone, 1,2-diaminopropane, acetic anhydride, alpha-methyl styrene, propylene carbonate and 1,2,3-trimethyl benzene, and dimethyl acetamide.

5. The method of claim 1, wherein the PHA enriched solvent is decolorized with activated carbon or activated clay.

6. The method of claim 1, wherein the biomass is a PHA-producing microorganism.

7. The method of claim 1, wherein the biomass is derived from a plant.

8. The method of claim 1, wherein the biomass is derived from plant stems, leaves, flowers, fruits, seeds, or roots.

9. The method of claim 1 wherein the biomass is corn stover, switchgrass or sugarcane.

10. The method of claim 1, wherein the biomass is oil-bearing seeds.

11. The method of claim 10, wherein the seeds are from canola, rapeseed, safflower, soybean or sunflower.

12. The method of claim 1, wherein the PHA is dissolved at a temperature between 90° C. and 180° C.

13. The method of claim 1 wherein the PHA concentration in the PHA-enriched solvent is between 1% and 40% w/v.

14. The method of claim 1, wherein the PHA is dissolved with a solvent comprising a mixture of PHA-good solvents.

15. The method of claim 1, wherein the PHA is separated from the PHA-enriched solvent via precipitation or solvent evaporation.

16. The method of claim 15, wherein PHA is precipitated by addition of a PHA-poor solvent.

17. A method for recovering PHA from biomass comprising:

providing biomass containing PHA;

dissolving PHA with a non-halogenated PHA-good solvent to produce PHA-enriched solvent and residual biomass materials;

separating the residual biomass materials from the PHA-enriched solvent;

precipitating PHA polymer from the PHA-enriched solvent by adding a PHA-poor solvent; and recovering the precipitated PHA polymer, wherein:

the PHA is selected from the group consisting of poly (hydroxybutyrate-co-hydroxyvalerate (PHBV), poly(3-hydroxybutyrate-co-4-hydroxybutyrate) (P3HB4HB), and polymers and copolymers of hydroxyterminated polyhydroxybutyrate (PHB-OH); and when the PHA is 3HB4HB or PHB-OH, the PHA good solvent is selected from the group consisting of: cyclic and acyclic R'—OH alcohols where R'=$C_4$–$C_{10}$, dimethyl glutarate, dimethyl adipate, isobutyl acetate, ethyl lactate, isoamyl acetate, benzyl acetate, 2-methoxy ethyl acetate, tetrahydrofurfuryl acetate, propyl propionate, pentyl propionate, butyl butyrate, isobutyl isobutyrate, ethyl butyrate, ethyl valerate, methyl valerate, benzyl benzoate, methyl benzoate, methyl propionate, allyl alcohol, tetrahydrofurfuryl alcohol, furfuryl alcohol, ethyl benzene, 1,3-dimethoxybenzene, cumene, benzaldehyde, 2-furaldehyde, 1,2-propanediol, 1,2-diaminopropane, ethylene glycol diethyl ether, 1,2,3-trimethylbenzene, 1,2,4-trimethylbenzene, 1,3-dioxane, 1-nitropropane, toluene-2,4-diisocyanate, acetic acid, acrylic acid, acetic anhydride, alpha-methyl styrene, propylene carbonate, methyl isobutyl ketone, methyl n-amyl ketone, 5-methyl-2-hexanone, and acetophenone, dimethyl acetamide;

and when the PHA is PHBV, the PHA-good solvent is selected from the group consisting of cumene, benzaldehyde, 2-furaldehyde, toluene-2,4-diisocyanate, alpha-methylstyrene, acetic acid, acrylic acid, acetic anhydride, 1,2-diaminopropane, 1-nitropropane, and an amyl alcohol mixed isomeric solution comprising 1-pentanol, 2-methyl-1-butanol, and 3-methyl-1-butanol; and the PHA-poor solvent is selected from solvents which dissolve less than 1% of the PHA at temperatures less than their boiling points.

18. The method of claim 17, wherein the PHA-poor solvent is selected from the group consisting of water, $R_1$—OH alcohols where $R_1$=$C_1$–$C_4$, $R_2$—$COOR_3$ esters where $R_2$=H or $C_1$–$C_3$ and $R_3$=$C_1$–$C_5$, and $C_5$–$C_{16}$ alkanes.

19. The method of claim 17, wherein the PHA is PHBV, and the PHA-good solvent is selected from the group consisting of cumene, benzaldehyde, 2-furaldehyde, toluene-2,4-diisocyanate, alpha-methylstyrene, acetic acid, acrylic acid, acetic anhydride, 1,2-diaminopropane, 1-nitropropane, and an amyl alcohol mixed isomeric solution comprising 1-pentanol, 2-methyl-1-butanol, and 3-methyl-1-butanol.

20. The method of claim 17, wherein the PHA is P3HB4HB copolymer and the PHA-good solvent is selected from the group consisting of ethyl butyrate, propyl propionate, tetrahydrofurfuryl acetate, methyl propionate, methyl n-valerate, ethyl valerate, 1-butanol, 2-methyl-1-butanol, 3-methyl-1-butanol, 1-pentanol, 3-pentanol, amyl alcohol, 1-hexanol, tetrahydrofurfuryl alcohol, methyl amyl ketone, methyl isobutyl ketone, acetophenone, 1,2-diaminopropane, acetic anhydride, alpha-methyl styrene, propylene carbonate and 1,2,3-trimethyl benzene, and dimethyl acetamide.

21. The method of claim 17, wherein the PHA is a polymer or copolymer of hydroxyterminated PHB and the PHA-good solvent is selected from the group consisting of tetrahydrofurfuryl acetate, methyl n-valerate, amyl alcohol, 1-hexanol, tetrahydrofurfuryl alcohol, acetophenone, methyl amyl ketone, 1,2-diaminopropane, acetic anhydride, alpha-methyl styrene, propylene carbonate and 1,2,3-trimethyl benzene, and dimethyl acetamide.

22. The method of claim 17, wherein the PHA-poor solvent is selected from the group consisting of methanol, ethanol, n-propanol, iso-propanol, n-butanol, heptane, octane, and hexadecane.

23. The method of claim 17, wherein the biomass is a PHA-producing microorganism.

24. The method of claim 17, wherein the biomass is derived from a plant.

25. The method of claim 17, wherein the biomass is derived from plant stems, leaves, flowers, fruits, seeds or roots.

26. The method of claim 17, wherein the biomass is corn stover, switchgrass or sugarcane.

27. The method of claim 17, wherein the biomass is an oil-bearing seed.

28. The method of claim 27, wherein the seeds are from canola, rapeseed, safflower, soybean, or sunflower.

29. The method of claim 17, wherein the PHA is dissolved at a temperature between 90° C. and 180° C.

30. The method of claim 17, wherein the PHA concentration in the PHA-enriched solvent is between 1% and 40% w/v.

31. The method of claim 17, wherein the PHA-good solvent comprises a mixture of PHA-good solvents.

32. The method of claim 17, wherein the PHA is dissolved with a solvent comprising a mixture of a PHA-good solvent and a PHA-poor solvent.

33. The method of claim 17, wherein the PHA-poor solvent is immiscible with the PHA-good solvent.

34. The method of claim 17, wherein the PHA-poor solvent is water.

35. The method of claim 17, wherein the PHA-poor solvent is miscible with the PHA-good solvent.

36. The method of claim 17, wherein the PHA-poor solvent comprises a mixture of PHA-poor solvents.

37. The method of claim 17, wherein the PHA-poor solvent comprises a mixture of a PHA-good solvent and a PHA-poor solvent.

38. A method for recovering PHA from oil-bearing seeds comprising:

provee seeds containing PHA;

co-dissolving the PHA and oil with a non-halogenated solvent to produce a PHA-enriched solvent/oil mixture and residual biomass materials;

separating the residual biomass materials from the PHA-enriched solvent/oil mixture; and separating the PHA from the PHA-enriched solvent/oil mixture; wherein the PHA is selected from the group consisting of poly(hydroxybutyrate-cohydroxyvalerate (PHBV), poly(3-hydroxybutyrate-co-4-hydroxybutyrate) (3HB4HB), and polymers and copolymers of hydroxyterminated polyhydroxybutyrate (PHB-OH); and when the PHA is 3HB4HB or PHB-OH, the solvent is selected from the group consisting of: cyclic and acyclic R'—OH alcohols where $R'=C_4-C_{10}$, allyl alcohol, tetrahydrofurfuryl alcohol, furfuryl alcohol, cumene, benzaldehyde, 2-furaldehyde, 1,2-propanediol, 1,2-diaminopropane, ethylene glycol diethyl ether, 1-nitropropane, toluene-2,4-diisocyanate, acetic acid, acrylic acid, acetic anhydride, alpha-methylstyrene, methyl isobutyl ketone, methyl n-amyl ketone, 5-methyl-2-hexanone, acetophenone, dimethyl glutarate, dimethyl adipate, ethyl benzene 1,3-dimethoxybenzene, 1,2,3-trimethylbenzene, 1,2,4-trimethylbenzene, propylene carbonate, isobutyl acetate, ethyl lactate, isoamyl acetate, benzyl acetate, 2-methoxy ethyl acetate, tetrahydrofurfuryl acetate, propyl propionate, pentyl propionate, butyl butyrate, isobutyl isobutyrate, ethyl butyrate, ethyl valerate, methyl valerate, benzyl benzoate, and methyl benzoate;

and when the PHA is PHBV, the solvent is selected from the group consisting of cumene, benzaldehyde, 2-furaldehyde, toluene-2,4-diisocyanate, alpha-methylstyrene, acetic acid, acrylic acid, acetic anhydride, 1,2-diaminopropane, 1-nitropropane, and an amyl alcohol mixed isomeric solution comprising 1-pentanol, 2-methyl-1-butanol, and 3-methyl-1-butanol.

39. The method of claim 38, wherein the PHA and oil are codissolved with a solvent selected from R'—OH alcohols where $R'=C_4-C_{10}$.

40. The method of claim 38, wherein the solvent is an amyl alcohol mixed isomeric solution comprising 1-pentanol, 2-methyl-1-butanol, and 3-methyl-1-butanol.

41. The method of claim 38, wherein the solvent is selected from the group consisting of methyl isobutyl ketone, methyl n-amyl ketone, 5-methyl-2-hexanone, and acetophenone.

42. The method of claim 38, wherein the solvent comprises a mixture of solvents.

43. The method of claim 38, wherein the PHA is separated from the PHA-enriched solvent/oil mixture by precipitation.

44. The method of claim 38, wherein the PHA is precipitated by reducing the temperature of the PHA-enriched solvent/oil mixture until PHA precipitation occurs.

45. The method of claim 38, wherein the oil is extracted from the PHA enriched solvent/oil mixture prior to separating the PHA.

46. The method of claim 1, wherein the solvent is selected from the group consisting of: cyclic and acyclic R'—OH alcohols where $R'=C_4-C_{10}$.

47. The method of claim 1, wherein the solvent is an amyl alcohol mixed isomeric solution comprising 1-pentanol, 2-methyl-1-butanol, and 3-methyl-1-butanol.

48. The method of claim 1, wherein the solvent is selected from the group consisting of isobutyl alcohol, 1-butanol, 2-methyl-1-butanol, 3-methyl-1 butanol, 1-pentanol, 3-pentanol, amyl alcohol, allyl alcohol, hexanol, heptanol, octanol, cyclohexanol, 2-ethylhexanol, tetrahydrofurfuryl alcohol, furfuryl alcohol, benzyl alcohol, 1,2-propanediol, and allyl alcohol.

49. The method of claim 1, wherein the solvent is selected from the group consisting of cumene, benzaldehyde, 2-furaldehyde, toluene-2,4-diisocyanate, and alpha-methylstyrene.

50. The method of claim 1, wherein the solvent is selected from the group consisting of acetic acid, acrylic acid, and acetic anhydride.

51. The method of claim 1, wherein the solvent is selected from the group consisting of 1,2-diaminopropane and 1-nitropropane.

52. The method of claim 1, wherein the solvent is selected from the group consisting of methyl isobutyl ketone, methyl n-amyl ketone, 5-methyl-2-hexanone, and acetophenone.

53. The method of claim 17, wherein the solvent is selected from the group consisting of: cyclic and acyclic R'—OH alcohols where $R'=C_4-C_{10}$.

54. The method of claim 17, wherein the solvent is an amyl alcohol mixed isomeric solution comprising 1-pentanol, 2-methyl-1-butanol, and 3-methyl-1-butanol.

55. The method of claim 17, wherein the solvent is selected from the group consisting of isobutyl alcohol, 1-butanol, 2-methyl-1-butanol, 3-methyl-1 butanol, 1-pentanol, 3-pentanol, amyl alcohol, allyl alcohol, hexanol, heptanol, octanol, cyclohexanol, 2-ethylhexanol, tetrahydrofurfuryl alcohol, furfuryl alcohol, benzyl alcohol, 1,2-propanediol, and allyl alcohol.

56. The method of claim 17, wherein the solvent is selected from the group consisting of cumene, benzaldehyde, 2-furaldehyde, toluene-2,4-diisocyanate, and alpha-methylstyrene.

57. The method of claim 17, wherein the solvent is selected from the group consisting of acetic acid, acrylic acid, and acetic anhydride.

58. The method of claim 17, wherein the solvent is selected from the group consisting of 1,2-diaminopropane and 1-nitropropane.

59. The method of claim 17, wherein the solvent is selected from the group consisting of methyl isobutyl ketone, methyl n-amyl ketone, 5-methyl-2-hexanone, and acetophenone.

60. The method of claim 38, wherein the solvent is selected from the group consisting of isobutyl alcohol, 1-butanol, 2-methyl-1-butanol, 3-methyl-1 butanol, 1-pentanol, 3-pentanol, amyl alcohol, allyl alcohol, hexanol, heptanol, octanol, cyclohexanol, 2-ethylhexanol, tetrahydrofurfuryl alcohol, furfuryl alcohol, benzyl alcohol, 1,2-propanediol, and allyl alcohol.

61. The method of claim 38, wherein the solvent is selected from the group consisting of cumene, benzaldehyde, 2-furaldehyde, toluene-2,4-diisocyanate, and alpha-methylstyrene.

62. The method of claim 38, wherein the solvent is selected from the group consisting of acetic acid, acrylic acid, and acetic anhydride.

63. The method of claim 38, wherein the solvent is selected from the group consisting of 1,2-diaminopropane and 1-nitropropane.

* * * * *

UNITED STATES PATENT AND TRADEMARK OFFICE
CERTIFICATE OF CORRECTION

| | | |
|---|---|---|
| PATENT NO. | : 6,043,063 | Page 1 of 1 |
| APPLICATION NO. | : 09/060121 | |
| DATED | : March 28, 2000 | |
| INVENTOR(S) | : Devdatt L. Kurdikar et al. | |

It is certified that error appears in the above-identified patent and that said Letters Patent is hereby corrected as shown below:

Claim 12, Column 15, line 6, replace "90°C." with --90°C--.
Claim 29, Column 16, line 48, replace "90°C." with --90°C--.

Signed and Sealed this

Twenty-first Day of August, 2007

JON W. DUDAS
*Director of the United States Patent and Trademark Office*